United States Patent [19]
Sydor et al.

[11] Patent Number: 5,484,392
[45] Date of Patent: Jan. 16, 1996

[54] WRIST SUPPORT AND WRIST SUPPORT STAY

[75] Inventors: Robin M. Sydor, St. Paul; Thomas M. Grimm, Robbinsdale, both of Minn.

[73] Assignee: Ergodyne Corporation, St. Paul, Minn.

[21] Appl. No.: 355,513

[22] Filed: Dec. 14, 1994

Related U.S. Application Data

[62] Division of Ser. No. 146,301, Nov. 2, 1993, Pat. No. 5,397,296.

[51] Int. Cl.$^6$ .................................................. A61F 13/00
[52] U.S. Cl. .................................. 602/5; 602/21; 2/255; 2/258
[58] Field of Search .................................. 602/20, 21, 22, 602/5, 62, 63, 64, 18, 19, 6; 2/161.2, 166, 255, 256, 258; 273/189 D, 189 A; 473/62

[56] References Cited

U.S. PATENT DOCUMENTS

| | | | |
|---|---|---|---|
| D. 286,073 | 10/1986 | Russell | D24/64 |
| 2,022,883 | 12/1935 | Gee | 128/89 |
| 2,794,638 | 6/1957 | Risher et al. | 273/54 |
| 3,030,633 | 4/1962 | Chalfin | 2/258 |
| 3,238,939 | 3/1966 | Stubbs | 128/165 |
| 3,276,041 | 10/1966 | Jonas | 2/258 |
| 3,327,703 | 6/1967 | Gamm | 128/77 |
| 3,351,954 | 11/1967 | Chalfin et al. | 2/255 |
| 3,512,776 | 5/1970 | Thomas, Sr. | 273/54 |
| 3,533,407 | 10/1970 | Smith | 128/165 |
| 3,598,408 | 8/1971 | Kloer | 273/54 |
| 3,703,171 | 11/1972 | Schiavitto | 128/80 |
| 3,728,738 | 4/1973 | Andolino | 2/161 |
| 3,815,908 | 6/1974 | Hashimoto | 273/54 |
| 4,183,098 | 1/1980 | Knowles, Jr. | 2/16 |
| 4,309,991 | 1/1982 | DeMarco | 128/165 |
| 4,366,812 | 1/1983 | Nuzzo | 128/77 |
| 4,517,968 | 5/1985 | Greene et al. | 128/80 |
| 4,584,993 | 4/1986 | Nelson | 128/77 |
| 4,776,327 | 10/1988 | Russell | 128/87 |
| 4,790,034 | 12/1988 | Pass | 2/255 X |
| 4,852,556 | 8/1989 | Groiso | 128/87 |
| 5,014,689 | 5/1991 | Meunchen et al. | 128/77 |
| 5,267,952 | 12/1993 | Gardner . | |
| 5,366,438 | 11/1994 | Martin, Sr. | 602/5 |

*Primary Examiner*—Richard J. Apley
*Assistant Examiner*—Beverly M. Flanagan
*Attorney, Agent, or Firm*—Merchant, Gould, Smith, Edell, Welter & Schmidt

[57] ABSTRACT

A wrist support (10) includes a base member (11) of a flexible material adapted to be formed into a tubular sleeve. A stay (30) is formed from a resilient material and includes a support member having first and second sides, a top and bottom and a plurality of slits wherein the support member provides support and the slits allow for additional flexibility. Further provided is a means for operatively connecting a stay proximate the base member. A loop member 17 is operatively connected to the base member 11 and mating member 13 is also operatively connected to the base member 11 at an end opposite the loop member. The mating member has a connecting element 13a operatively connected to a tab element 13b. The tab element 13b is wider than the length of the loop member 17 and has to be deformed to pass through the slot to the opening 17a and the loop member 17.

7 Claims, 3 Drawing Sheets

WRIST SUPPORT AND WRIST SUPPORT STAY

This is a division of application Ser. No. 08/146,301, filed Nov. 2, 1993, which application is incorporated herein by reference, and is now U.S. Pat. No. 5,397,296.

BACKGROUND OF THE INVENTION

1. Field of the Invention

This invention relates generally to a wrist support and more particularly to a wrist support which requires less awkward hand manipulation to use and which utilizes a one-piece stay which is designed to allow controlled flexion as well as lateral movement while still providing support.

2. Description of the Prior Art

Carpal tunnel syndrome is caused when the median nerve that runs through the wrist is subjected to excess pressure and stress. This often occurs in the workplace because of repetitive operations being performed. Once the symptoms of pain and tingling appear in the wrist, the carpal tunnel syndrome frequently worsens and may even permanently damage the nerve. Numerous hand braces have been utilized which limit the movement of the hand relative to the wrist. That is, the brace limits flexion and extension of the hand and also limits the ulnar and radial deviation of the hand. It is also important for the brace to have a "memory" to urge the wrist back to a neutral position.

While a number of braces which exist have been useful in preventing carpal tunnel syndrome there are problems associated with the prior art devices. The prior art braces typically use multiple stays or multiple channel construction. This provides for a more complex and costly brace to manufacture. Still further, the braces typically require that the brace be wrapped around the wearer's hand before it is secured in position. This manipulation can cause the wearer problems, especially if the wearer is already suffering from carpal tunnel syndrome where manipulation of the hand is painful. Further, it has been difficult to find a support stay which is cost effective and provides adequate support and still provides for a suitable amount of flexion as the wrist is moved. Also, a number of stays have a sufficient amount of creep such that after repeated flexing, they do not return to their original position.

The present invention addresses the problems associated with the prior art devices and provides a wrist support which is easily slipped on the hand without requiring substantial awkward manipulation. Further, the wrist support incorporates a single one-piece stay of a suitable material that has a plurality of slits formed in the stay to allow additional flexion and twisting where appropriate.

SUMMARY OF THE INVENTION

The present invention is a wrist support including a base member of a flexible material adapted to be formed into a tubular sleeve. A stay includes a support member having first and second sides, a top and a bottom. The support member is a thermoplastic material or metal having a memory, whereby after flexing, the support returns to its original configuration. A plurality of slits are formed in the support member, wherein the support member provides support and the slits allow for additional flexibility. Means are also provided for operatively connecting the stay proximate the base member. In a preferred embodiment, the support member has an opening in its interior so that while in use, the opening releases compression of the median nerve of a wearer. In still another preferred embodiment, there are additional plurality of slits provided in the support member.

In another embodiment of the invention, the invention is a stay having a support member having first and second sides, a top and a bottom. The support member is a thermoplastic material or metal having a memory, whereby after flexing, the support returns to its original configuration. A plurality of slits are formed in the support member, wherein the support member provides support and the slits allow for additional flexibility.

In another embodiment of the invention, the invention is a wrist support having a base member of a flexible material adapted to be formed into a tubular sleeve. The base member has a first end and a second end. The base member is stretched in a circumferential direction around a wrist and the base member is moveable between a first condition and a second, stretched condition. There is also provided means for securing the base member in a first tubular position which is sized to allow easy insertion of a wearer's hand while in the first tubular position and after insertion over the wearer's hand to be cinched to a second tubular position, smaller than the first tubular position when the base member is in the stretched condition.

DETAILED DESCRIPTION OF THE PREFERRED EMBODIMENT

Figure 1:
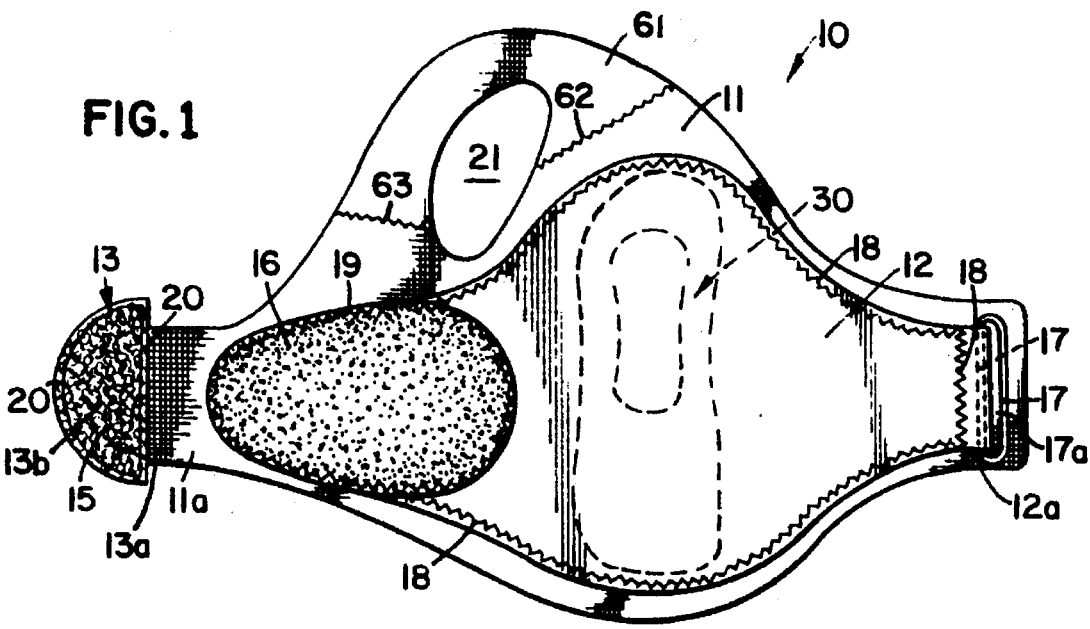
FIG. 1 is a top plan view of the wrist support in accordance with the present invention shown in an unwrapped configuration.
Figure 2:
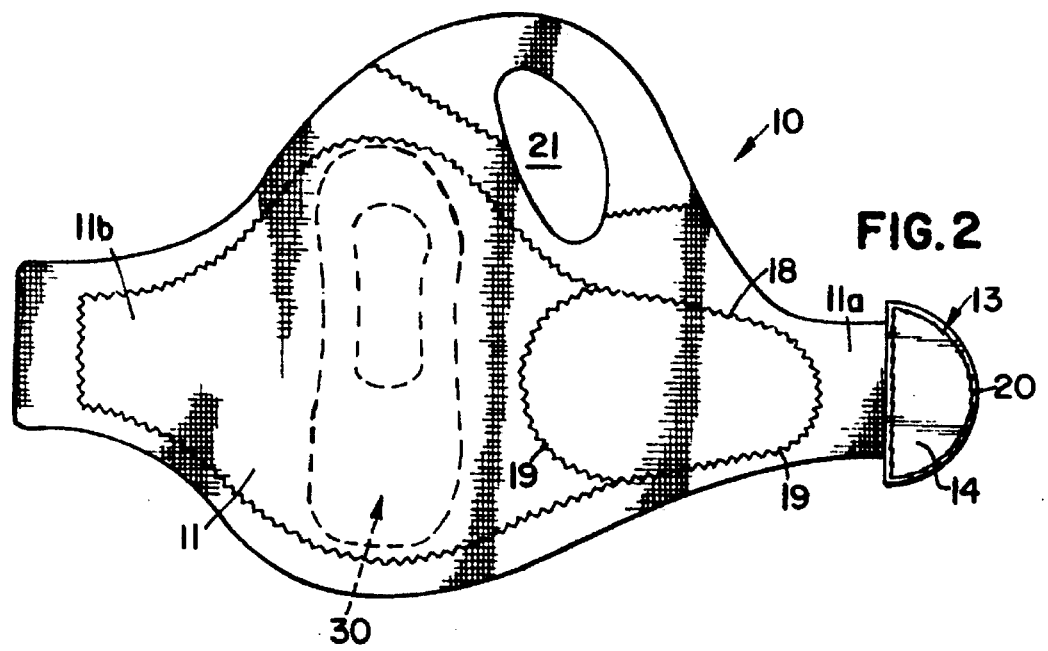
FIG. 2 is a bottom plan view of the wrist support shown in FIG. 1.

Referring to the drawings, wherein like numerals represent like parts throughout the several views, there is generally disclosed at 10 a wrist support. The wrist support 10 includes a base member 11 which is constructed of a flexible material adapted to be formed into a tubular sleeve. The base member 11 may be any suitable material such as Neoprene®. In viewing FIG. 2, the base member 11 comprises an enlarged central region and a first end area 11a and a second end area 11b. A stay 30, to be described in more detail hereafter, is placed in the central region of the base member 11 and vinyl overlay 12 is operatively connected to the base member 11 by suitable means such as stitching 18 or gluing or sonic welding. The perimeter stitching 18 is sufficient to secure in place the stay 30. This is because the stitching 18 at both the top and bottom of the central region is curved and curves around the stay 30 sufficient to form a pocket to not allow the stay 30 be displaced. The vinyl overlay 12 has an end 12a that is folded underneath and secured by the stitching 18 also. This leaves a free end in the form of a loop through which a metal loop 17 is secured. The loop could also be plastic, TPE or other suitable material. In construction, the end 12a is placed through the opening 17a of the metal loop 17 and tucked underneath and stitched by stitching 18, thereby providing the loop which secures the metal loop 17. A generally oval piece of loop material 16 is operatively connected to the vinyl overlay 12 by suitable means such as stitching 19. There is a U-shaped section where stitching 19 and 18 overlaps. A mating member generally disclosed at 13 is operatively connected to first end area 11a of the base member by a connecting element 13a, which in a preferred embodiment is just a continuation of the end 11a. A tab element 13b is operatively connected to the connecting element 13a. Preferably, the inner portion of the tab 13 is simply a continuation of the connecting element 13a, but of a larger width. A semi-circular portion of hook material 15 is operatively connected to the top portion of the tab element 13b and a plastic overlay 14 is operatively connected to the bottom portion of the tab element 13b. Preferably, both the hook material 15 and overlay 14 are connected by stitching 20. The hook and loop material may be any suitable material, such as Velcro®. It is also understood that the hook and loop material could be reversed. A curved strip of material 61 is connected to the top of the base member 11 to form a thumb hole 21. The material is connected by means of stitching 62 and 63. The material 61 is of a material similar to base member 11. Alternately, instead of attaching the material 61 the base member 11 could be extended and a hole cut out to form the thumb hole 21.

Figure 3:
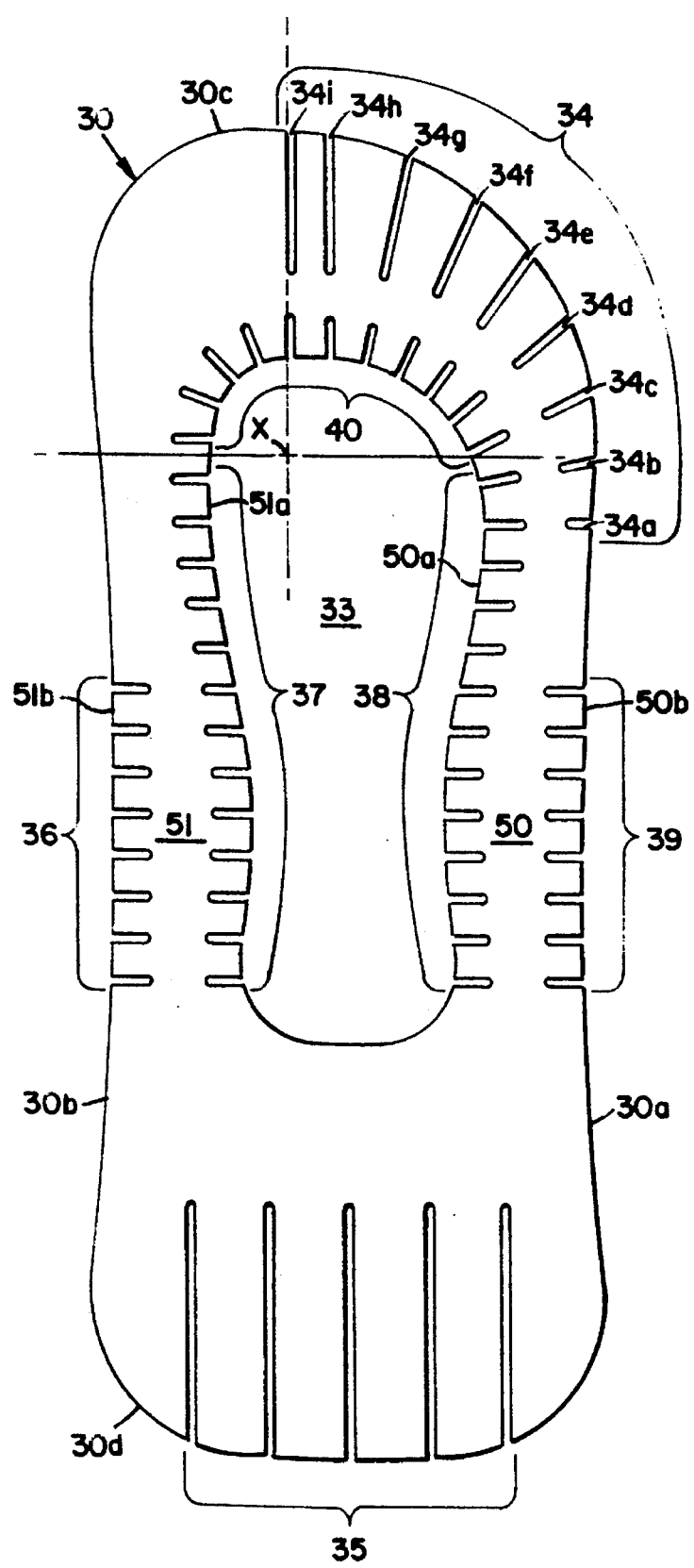
FIG. 3 is a top plan view of the stay used in the wrist support shown in FIG. 1.

The stay 30 is shown in an enlarged view in FIG. 3. Typically, the stay 30 would be approximately four inches in height and 1.63 inches in width at its base. The thickness of the generally planar stay 30 is approximately 0.070 inches. The stay 30 is made from a strong flexible material with a memory that is cost effective when mass produced. The memory is necessary so that the stay 30 will always return, after flexing, to its original configuration, which in this embodiment is a flat planar position. The required stiffness and memory to do this is required so that the wrist is forced to come back to an original neutral position. One suitable thermoplastic material would be nylon 6/6 which has the required stiffness for support as well as a good memory to return to its originally flat planar position. Other suitable nylons, such as nylon 6, nylon 6/12, or other suitable plastics or metals may also be used. Still further, the material exhibits very little creep so that the original configuration is not distorted after repeated flexing.

The stay 30 has a first side 30a, second side 30b, top 30c and bottom 30d. A generally elongate opening 33 is formed in the stay 30. The opening 33 is sized and configured to be positioned over the median nerve of a wearer so as to release compression of the median nerve when worn by the wearer of the wrist support 10. The opening 33 is in the general shape of an oval having a length of approximately 2.06 inches with an enlarged area at one end having a width of 0.88 inches and a width of 0.62 inches at the other end. The opening 33 and first side 30a generally define a first column 50 and the opening 33 and second side 30b generally describe a second column 51. The first column 50 has an inner edge 50a and an outer edge 50b. Similarly, the second column 51 has an inner edge 51a and an outer edge 51b. A first plurality of slits 38 are formed in the stay 30 and are generally parallel to each other and perpendicular to the inner edge 50a. A second plurality of slits 39 are formed in the stay 30 and are generally parallel to each other and perpendicular to the outer edge 50b. A third plurality of slits 37 are formed in the stay 30 and are generally parallel to each other and perpendicular to the inner edge 51a. A fourth plurality of slits 36 are formed in the stay 30 and are generally parallel to each other and perpendicular to the outer edge 51a. A reinforcing rib (not shown) may also be formed generally along the first column 50 and another reinforcing rib (not shown) may be formed along the second column 51. The reinforcing ribs would provide additional support so that the base of the support does not break.

A fifth plurality of slits 35 are formed proximate the bottom 30d of the stay. A sixth plurality of slits 34 are formed proximate the top 30c of the support 30. Finally, a seventh plurality of slits 40 are formed proximate the top edge of the opening 33 and extend between the slits 37 and slits 38.

Each of the slits in the plurality of slits 36, 37, 38, 39 and 40 are typically 0.125 inches in length and have a width 0.025 inches and their center lines are spaced approximately 0.013 inches from the adjacent slit. The slits have a curved end.

The slits 35 are 0.03 inches in width but have a length of 0.75 inches and their center lines are spaced at approximately a distance of 0.23 inches. The slits 34 begin at one end with a length of approximately 0.125 inches and gradually increase at the other end of the set of slits to 0.44 inches. If slits 34a and 34h were extended, they would intersect and form an angle of approximately 90°. Therefore, it can be seen that the spacings between the slits 34a through 34h is approximately 13°. The slit 34i is approximately parallel to slit 34h and is spaced at a distance of 0.12 inches.

The fours sets of slits 36, 37, 38, and 39 allow for the support 30 to be twisted. The set of slits 35 helps the support 30 to roll and bend with the wearer's wrist joint. The set of slits 34 allow for additional flexibility so that when the wearer's fingers are using a pinching motion, there is additional flexibility of the support 30. Similarly, the set of slits 40 accentuate the flexibility available when the fingers are in the pinching motion.

As can be seen in viewing FIG. 3, the support 30 is in the general shape of a rectangle. Three of the corners are formed with a ½ inch radius. However, the portion of the support which is proximate the wearer's thumb, which is in the upper right hand portion of FIG. 3, is cut away and the top 30c and side 30a form an arcuate edge whereby the support 30 is shaped and configured to allow more flexibility in the area proximate the wearer's thumb. The arcuate edge is formed with a radius of approximately one inch from the point X shown in FIG. 3.

Figure 4:
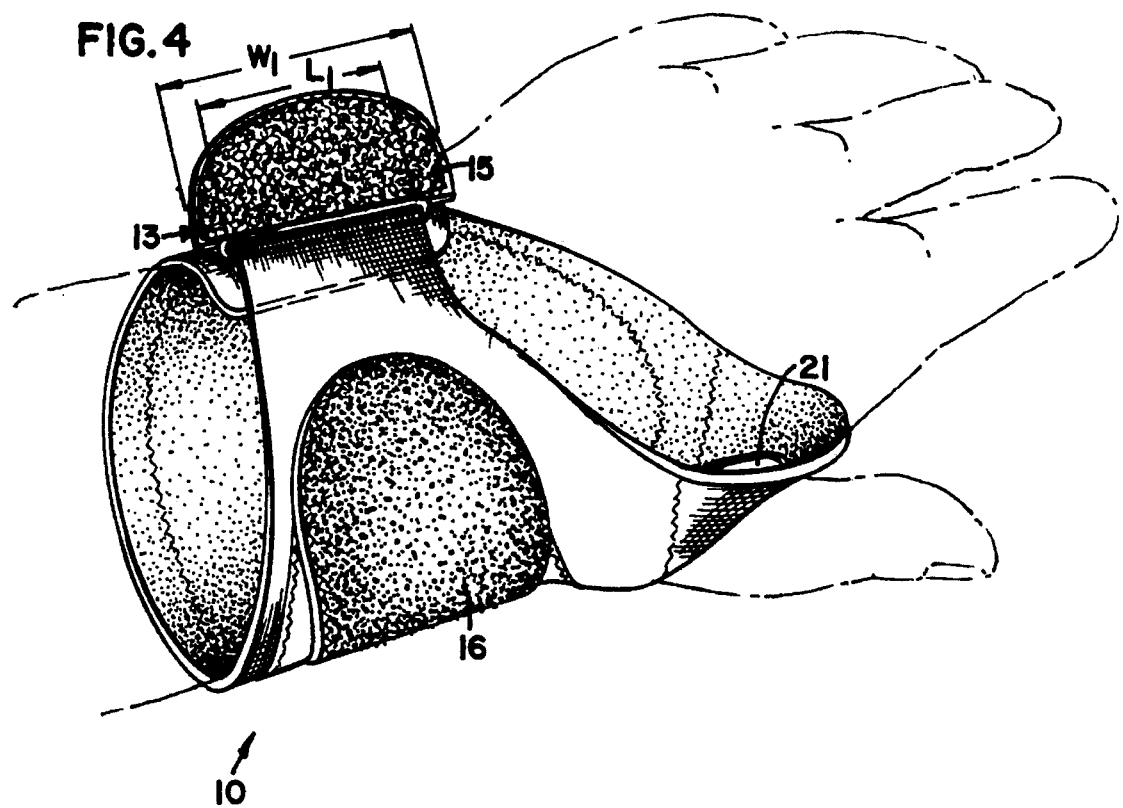
FIG. 4 is a perspective view of the wrist support shown in FIG. 1, shown positioned on a wearer's hand and in a loose or first condition.
Figure 5:
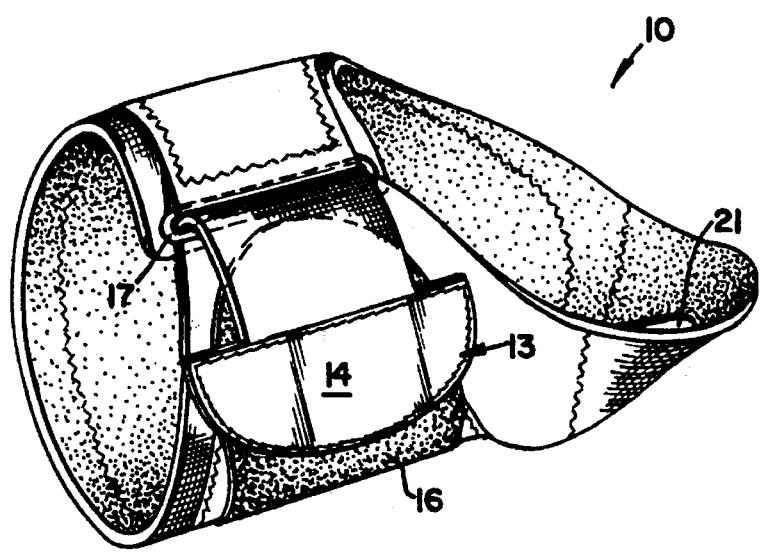
FIG. 5 is a perspective view of the wrist support shown in FIG. 4 shown in a second or stretched/tightened condition.

In use, the base member 10 is formed in a generally tubular shape and the tab 13b is forced through the opening 17a of the metal loop 17. The tab 13b is of a material that has a width W1 which is greater than the length L1 of the opening 17a. The tab 13b, however, is deformable and can be made to slide through the opening 17a. The connecting element 13a has a width less than the length $L_1$ of the opening 17a. Then, once through the opening 17a, the tab 13b expands to its original shape and is secured in position. The support 10 is then in a first generally tubular shape and is in a first condition which is sized to be loose on the wearer. This condition is shown in FIG. 4. When the manipulation of the tab 13b through the opening 17a is accomplished, the wrist support 10 is not on the wearer. Therefore, the wearer has both hands to manipulate the tab 13b. Then it is an easy movement for the wearer to simply slide the tubular sleeve formed by the wrist support 10 over the wearer's hand. Then, the wearer grasps the tab 13b and pulls it back toward the loop material 16. This movement cinches the base member 11 as it stretches the base member 11 in a circumferential direction around the wrist of the wearer. The wrist support 10 is then in a stretched condition, and the hook material 15 is pressed against the loop material 16, thereby securing the support in the stretched condition. This is the condition shown in FIG. 5, without the hand being shown in phantom. This stretched condition is small than the first condition shown in FIG. 4 as the support has been cinched tight by the movement of the tab 13b around the loop 17 and back toward the loop material 16.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

We claim:

1. A stay, comprising:
   (a) a support member having first and second sides, a top and a bottom said support member formed of a material having a memory, whereby after flexing said support returns to its original configuration;
   (b) a plurality of slits formed in said support member, wherein said support member provides support and said slits allow for additional flexibility; and
   (c) said support member having an opening in its interior wherein said stay is adapted to overlie the wrist area of a wearer so that while in use, said opening releases compression of a median nerve of a wearer.

2. The stay of claim 1, wherein said opening, along with said first and second sides, define first and second columns, each column having an inner edge and an outer edge.

3. The stay of claim 2, wherein said plurality of first slits are proximate said outer edges.

4. The stay of claim 3, further comprising a plurality of second slits proximate said inner edges.

5. The stay of claim 4, further comprising a plurality of third slits formed proximate said bottom.

6. The stay of claim 5, further comprising a plurality of fourth slits formed proximate said top.

7. A stay, comprising:
   (a) a support member having first and second sides, a top and a bottom said support member formed of a material having a memory, whereby after flexing said support returns to its original configuration;
   (b) a plurality of slits formed in said support member, wherein said support member provides support and said slits allow for additional flexibility; and
   (c) said top and first side forming an arcuate edge wherein said stay support member is adapted to overlie the wrist area of a wearer and is shaped and configured to allow more flexibility in an area proximate a wearer's thumb.

* * * * *